(12) United States Patent
Zelen et al.

(10) Patent No.: US 11,419,748 B2
(45) Date of Patent: Aug. 23, 2022

(54) APPARATUS AND SYSTEM FOR EXTERNAL ORTHOPEDIC DEVICES

(71) Applicant: Zimmer, Inc., Warsaw, IN (US)

(72) Inventors: Charles M. Zelen, Warsaw, IN (US);
Orsa Britton, Warsaw, IN (US);
Kenneth D. Johannaber, Reno, NV (US); David A. Nolan, Fort Wayne, IN (US); Derek Dalbey, Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 793 days.

(21) Appl. No.: 16/038,840

(22) Filed: Jul. 18, 2018

(65) Prior Publication Data

US 2019/0021894 A1 Jan. 24, 2019

Related U.S. Application Data

(60) Provisional application No. 62/534,396, filed on Jul. 19, 2017.

(51) Int. Cl.
*A61F 5/01* (2006.01)
*A43B 7/00* (2006.01)
(Continued)

(52) U.S. Cl.
CPC .............. *A61F 5/0195* (2013.01); *A43B 3/34* (2022.01); *A43B 7/00* (2013.01); *A61B 5/112* (2013.01);
(Continued)

(58) Field of Classification Search
CPC .... A61F 5/0195; A61F 5/0111; A61F 5/0127; A43B 7/00; A43B 3/0005; A61B 5/112;
(Continued)

(56) References Cited

U.S. PATENT DOCUMENTS 5,357,696 A * 10/1994 Gray ..................... A43B 7/00
36/136
8,323,282 B2 * 12/2012 Taylor ................... A61B 17/62
606/59

(Continued)

FOREIGN PATENT DOCUMENTS

FR     2856283 A1 * 12/2004 ........... A61B 5/1036
GB     2519650 B  * 11/2015 ............ A61F 5/0111

OTHER PUBLICATIONS

Zdravkovic, Milan, et al., "Towards the Internet-of-Things platform for orthopaedics surgery—the smart external fixation device case studies", https://www.researchgate.net/publication/298215019, (Mar. 2016), 7 pgs.

*Primary Examiner* — Patrick Fernandes
(74) *Attorney, Agent, or Firm* — Schwegman Lundberg & Woessner, P.A.

(57) ABSTRACT

A stabilization device can determine a condition of a human foot and can include a body, a pad, and a sensor. The body can be coupleable to a human foot. The pad can be coupleable to a distal portion of the body, and the pad can be configured to interface with a walking surface. The sensor can be securable to one of the body and the pad and the sensor can be configured to produce a sensor signal as a function of a sensed condition of the stabilization device.

5 Claims, 10 Drawing Sheets

(51) Int. Cl.
   *A61B 5/00*    (2006.01)
   *A61B 5/11*    (2006.01)
   *A61B 17/72*   (2006.01)
   *A61B 17/62*   (2006.01)
   *A43B 3/34*    (2022.01)
   *A61B 5/103*   (2006.01)
   *G16H 40/67*   (2018.01)
   *G16H 20/30*   (2018.01)

(52) U.S. Cl.
   CPC ............ *A61B 5/6807* (2013.01); *A61B 5/746* (2013.01); *A61B 17/62* (2013.01); *A61B 17/7291* (2013.01); *A61F 5/0111* (2013.01); *A61F 5/0127* (2013.01); *A61B 5/0022* (2013.01); *A61B 5/1036* (2013.01); *A61B 2505/09* (2013.01); *A61B 2562/0219* (2013.01); *A61B 2562/0261* (2013.01); *G16H 20/30* (2018.01); *G16H 40/67* (2018.01)

(58) Field of Classification Search
   CPC ....... A61B 5/6807; A61B 5/746; A61B 17/62; A61B 17/7291; A61B 5/0022; A61B 5/1036; A61B 2505/09; A61B 2562/0219; A61B 2562/0261; G16H 20/30; G16H 40/67

See application file for complete search history.

(56) References Cited

U.S. PATENT DOCUMENTS

| | | | |
|---|---|---|---|
| 2002/0183673 A1* | 12/2002 | Naft | A61F 5/0125 602/16 |
| 2005/0172517 A1* | 8/2005 | Bledsoe | A43B 7/141 36/110 |
| 2013/0150755 A1* | 6/2013 | Kubiak | A61B 5/11 600/592 |
| 2014/0303540 A1* | 10/2014 | Baym | A61B 5/6812 602/23 |
| 2018/0214073 A1* | 8/2018 | Lewis | A61B 5/4842 |
| 2018/0317965 A1* | 11/2018 | Robinson | A61B 17/6425 |
| 2019/0231259 A1* | 8/2019 | Cohen | A61B 5/6812 |

* cited by examiner

APPARATUS AND SYSTEM FOR EXTERNAL ORTHOPEDIC DEVICES

CLAIM OF PRIORITY

This application claims the benefit of U.S. Provisional Patent Application Ser. No. 62/534,396, filed on Jul. 19, 2017, the benefit of priority of which is claimed hereby, and which is incorporated by reference herein in its entirety.

BACKGROUND

Patients with diabetes and other circulation issues may develop peripheral neuropathy (or lack of sensation of extremities). In some cases, these patients can be at a higher risk of ulcers, broken bones, and torn and elongated ligaments. Some of these patients having peripheral neuropathy can develop Charcot foot, or a weakening of the bones of the foot, which can lead to further or chronic injuries and in some cases frequent fractures of the bones of the foot. To address these conditions, stabilization devices, such as walking boots and external fixators, may be used following an injury or surgery and/or to prevent further injuries.

OVERVIEW

To illustrate the apparatuses and systems disclosed herein, the following non-limiting examples are provided:

Example 1 is a stabilization device configured to determine a condition of a human foot, the stabilization device comprising: a body coupleable to a human foot; a pad coupleable to a distal portion of the body, the pad configured to interface with a walking surface; and a sensor securable to one of the body and the pad, the sensor configured to produce a sensor signal as a function of a sensed condition of the stabilization device.

In Example 2, the subject matter of Example 1 optionally includes a pad sensor embedded within the pad and configured to produce a pad sensor signal as a function of a sensed condition of the pad.

In Example 3, the subject matter of Example 2 optionally includes wherein the pad sensor is one of an accelerometer, a force sensor, and a strain sensor.

In Example 4, the subject matter of any one or more of Examples 2-3 optionally include an indicator securable to one of the body and the pad, the indicator configured to produce a visual indication as a function of the sensor signal.

In Example 5, the subject matter of any one or more of Examples 1-4 optionally include the body further comprising: a boot releasably securable to a human foot, the pad coupleable to a distal portion of the boot.

In Example 6, the subject matter of any one or more of Examples 1-5 optionally include a pin configured to pass through a human tibia; a ring fixator securable to the human tibia by the pin; a foot plate disposable around a periphery of the foot; a rod coupleable to the foot plate and to the pad; a strut configured to couple the foot plate to the ring; and a strut sensor coupleable to the strut and configured to produce a strut sensor signal as a function of a condition of the strut.

In Example 7, the subject matter of Example 6 optionally includes the body further comprising: a wire securable to a medial portion of the foot plate and a lateral portion of the footplate; and a foot plate sensor coupleable to the wire and configured to produce a foot plate sensor signal as a function of a condition of the foot plate.

In Example 8, the subject matter of any one or more of Examples 6-7 optionally include the body further comprising: a second pin configured to pass through the human tibia; a second ring fixator securable to the human tibia by the second pin; a second wire securable to the ring fixator and the second ring fixator; a ring fixator sensor coupleable to the wire and configured to produce a ring fixator sensor signal as a function of a condition of one or more of the first ring fixator, the second ring fixator, and the second wire.

Example 9 is a stabilization system configured to determine a condition of a human foot, the system comprising: a stabilization device coupleable to a human foot and configured to interface with a walking surface; a sensor coupleable to the stabilization device, the sensor configured to produce a sensor signal as a function of a sensed condition of the stabilization device; and a controller in communication with the sensor and configured to determine a condition of the stabilization device as a function of the sensor signal.

In Example 10, the subject matter of Example 9 optionally includes the stabilization device further comprising: a boot coupleable to a human foot; a pad coupleable to a distal portion of the body, the pad configured to interface with a walking surface; and a pad sensor embedded within the pad and configured to produce a pad sensor signal as a function of a sensed condition of the pad sensor.

In Example 11, the subject matter of any one or more of Examples 9-10 optionally include an indicator securable to the stabilization device, the indicator configured to produce a visual indication as a function of the sensor signal.

In Example 12, the subject matter of any one or more of Examples 9-11 optionally include a remote device configured to interface with the controller and produce an output as a function of the sensor signal.

In Example 13, the subject matter of Example 12 optionally includes wherein the remote device is configured to wirelessly communicate with the controller.

In Example 14, the subject matter of any one or more of Examples 9-13 optionally include a pin configured to pass through a human tibia; a ring fixator securable to the human tibia by the pin; a foot plate disposable around a periphery of the foot; a rod coupleable to the foot plate and to the pad; a strut configured to couple the foot plate to the ring; and a strut sensor coupleable to the strut and configured to produce a strut sensor signal as a function of a condition of the strut.

In Example 15, the subject matter of any one or more of Examples 9-14 optionally include a wire securable to a medial portion of the foot plate and a lateral portion of the foot plate; and a foot plate sensor coupleable to the wire and configured to produce a foot plate sensor signal as a function of a condition of the foot plate.

In Example 16, the subject matter of any one or more of Examples 14-15 optionally include a second pin configured to pass through the human tibia; a second ring fixator securable to the human tibia by the second pin; a second wire securable to the ring fixator and the second ring fixator; a ring fixator sensor coupleable to the wire and configured to produce a ring fixator sensor signal as a function of a condition of one or more of the first ring fixator, the second ring fixator, and the second wire.

Example 17 is a method of analyzing a stabilization system for a human foot, the method comprising: producing a sensor signal from a sensor coupled to a stabilization system coupled to a human foot; and determining a condition of the stabilization system as a function of the sensor signal.

In Example 18, the subject matter of Example 17 optionally includes producing an indication signal as a function of the determined condition; and indicating the determined condition with an indicator secured to the stabilization system as a function of the indication signal.

In Example 19, the subject matter of any one or more of Examples 17-18 optionally include transmitting one or more of the sensor signal and the determined condition to a remote device.

In Example 20, the subject matter of Example 19 optionally includes transmitting one or more of the sensor signal and the determined condition from the remote device to a central device; analyzing one or more of the sensor signal and the determined condition by comparing one or more of the sensor signal and the determined condition to data of a central database; producing an instruction signal as a function of the analysis; and transmitting the instruction signal from the central device to the remote device.

Example 21 is a stabilization system configured to determine a condition of a human foot, the stabilization device comprising: a stabilization device coupleable to a human foot and configured to interface with a walking surface; a sensor coupleable to the stabilization device, the sensor configured to produce a sensor signal as a function of a sensed condition of the stabilization device; and a controller in communication with the sensor and configured to determine a condition of the stabilization device as a function of the sensor signal.

In Example 22, the subject matter of Example 21 optionally includes wherein: the controller is configured to determine an alignment of the human foot with respect to gravity as a function of the sensor signal.

In Example 23, the subject matter of any one or more of Examples 21-22 optionally include wherein: the controller is configured to determine an alignment of the foot with respect to gravity during a planting phase of a gate of the human foot as a function of the sensor signal.

In Example 24, the subject matter of any one or more of Examples 21-23 optionally include wherein: the controller is configured to determine one or more of flexion, extension, valgus shift, and varus shift of the human foot as a function of the sensor signal.

In Example 25, the subject matter of any one or more of Examples 21-24 optionally include wherein: the controller is configured to determine one or more of a quantity of steps, a distance of leg swing, and gate kinematics of the human foot as a function of the sensor signal.

In Example 26, the subject matter of any one or more of Examples 21-25 optionally include an indicator in communication with the controller, wherein the controller produces an indicator signal as a function of the sensor signal.

In Example 27, the subject matter of any one or more of Examples 21-26 optionally include wherein: the controller produces an indicator signal instructing the indicator to activate when the controller detects an off-axis load of the stabilization device as a function of the sensor signal.

In Example 28, the subject matter of any one or more of Examples 21-27 optionally include wherein: the controller collects and stores data based on the sensor signal.

In Example 29, the subject matter of any one or more of Examples 21-28 optionally include the sensor further comprising: a force sensor configured to produce a force signal as a function of a measured force of the stabilization device; and a gyroscope sensor configured to produce an orientation signal as a function of a measured orientation of the stabilization device.

In Example 30, the subject matter of Example 29 optionally includes wherein: the controller produces an indicator signal instructing the indicator to activate when the controller determines an off-axis load of the stabilization device as a function of the force signal and the orientation signal.

In Example 31, the subject matter of any one or more of Examples 29-30 optionally include wherein: the force sensor is configured to produce the force signal as a function of one or more of a static load and an impulse.

In Example 32, the device, assembly, or method of any one of or any combination of Examples 1-31 is optionally configured such that all elements or options recited are available to use or select from.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

In some cases stabilization devices, such as a walking boot and an external fixator, may be used following a surgery and/or to prevent further injuries. However, because some patients requiring a stabilization device have peripheral neuropathy, the patients may not possess the requisite ability to detect pain to prevent further or additional injuries, which can result in re-injury of the foot and/or breakage of the stabilization device. These problems may be exacerbated by patients having a body mass index that is relatively high, which can increase the forces and stresses applied to the foot of the patient.

The inventors have recognized, among other things, that sensors can be incorporated into a stabilization device, such as a boot or an external fixator, to detect conditions of the stabilization device and produce sensors signals as a function of the sensed condition or conditions. The inventors have further recognized that the sensor signals can be used to determine conditions of the patient's stabilization device and can be used to determine dynamics of a patient's gate as well as static loads experienced at the stabilization device. The collected data can be used to inform the patient and/or a physician of potentially harmful conditions, helping to prevent re-injury and helping to detect injuries early.

Figure 1A:
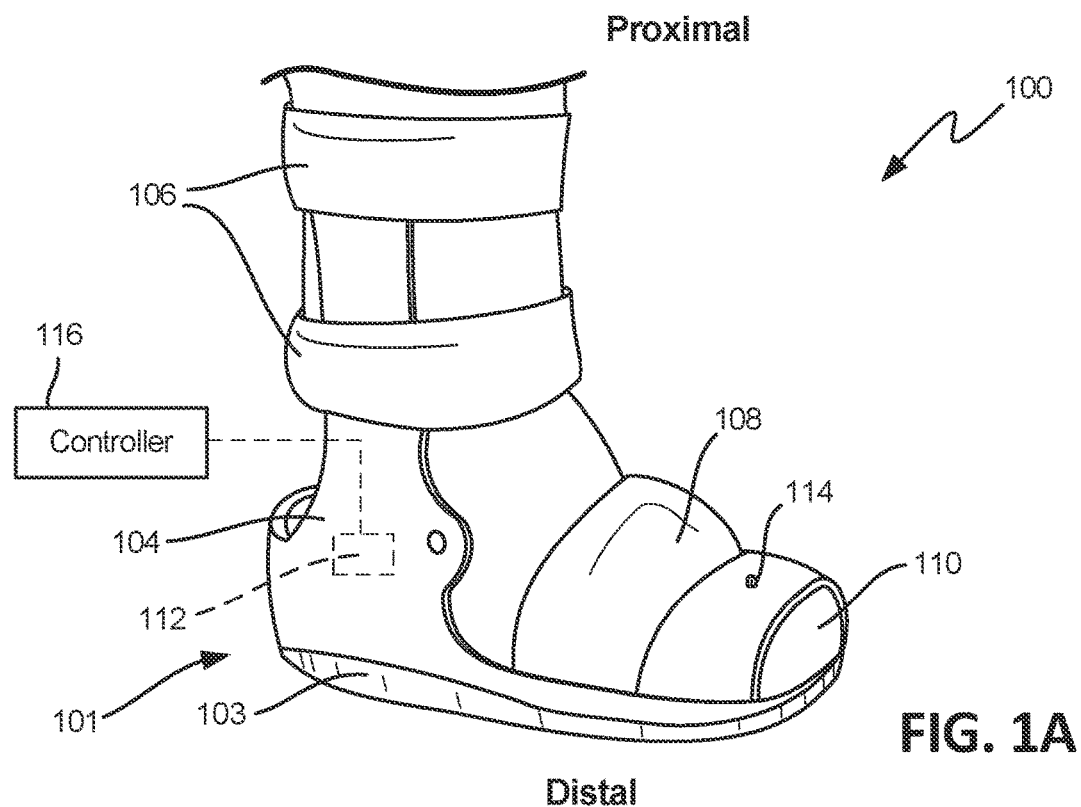
FIG. 1A illustrates a perspective view of a stabilization system, in accordance with at least one example of the present disclosure.
Figure 1B:
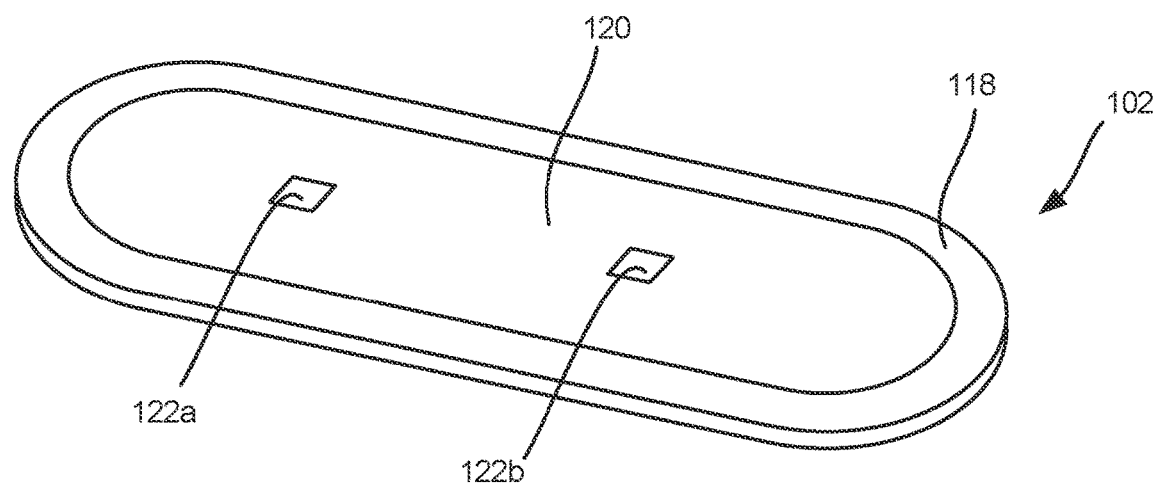
FIG. 1B illustrates a bottom view of a stabilization system, in accordance with at least one example of the present disclosure.

FIG. 1A illustrates a perspective view of stabilization system 100, in accordance with at least one example of the present disclosure. FIG. 1B illustrates a bottom view of stabilization system 100, in accordance with at least one example of the present disclosure. FIGS. 1A and 1B are discussed below concurrently.

Stabilization system 100 can include stabilization device 101, which can include pad 102, brace 104, straps 106, padding 108, and toe opening 110. Stabilization system 100 can further include sensor 112, indicator 114, and controller 116. Pad 102 can include contact portion 118, support portion 120, and sensors 122a and 122b.

Stabilization device 101 can be a walking boot or similar device configured to support the foot of a patient and configured to enable walking with an injury or walking to promote healing and/or prevent further injury. Sole 103 can be a flexible but resilient member coupled to a distal portion of brace 104. Sole 103 can be comprised of materials such as foams, rubbers, plastics, combinations thereof, and the like.

Brace 104 can be a semi-rigid member configured to provide medial and lateral support to a human foot and configured to couple sole 103 to padding 108 and straps 106. Brace 104 can be comprised of rigid materials, such as plastics, metals, composites, combinations thereof, and the like. Padding 108 can be a flexible and/or soft material such as foam, rubber, cotton, combinations thereof, and the like. Padding can surround the foot within stabilization device 101. Padding 108 can include toe opening 110, which can be sized to allow toes of the foot to extend from the stabilization device, in some examples.

Straps 106 can be wraps comprised of flexible material, such as cloth, plastics, rubbers and the like. Straps 106 can include a fastening mechanism, such as hook and loop fasteners, snaps, buckles, and the like, such that the fastening mechanism can be used to secure a stabilization device 101 to a distal portion of a patient's leg, in some examples.

Sensor 112 can be a sensor coupled to brace 104, as shown in FIG. 1A. However, sensor 112 can be coupled to any other part of stabilization device 101 in other examples. Sensor 112 can be a sensor configured to produce a sensor signal as a function of a sensed condition of stabilization device 101. Sensor 112 can be a force sensor, a strain sensor, a gyroscope, a displacement sensor, and the like. Though only one of sensor 112 is shown in FIG. 1A, stabilization device 101 can include multiple sensors mounted on a variety of parts, in some examples. In one example, sensor 112 can be mounted on a lateral side of brace 104 and a second sensor 112 can be mounted on a medial side of brace 104.

Indicator 114 can be a device configured to produce a visual, audible, or haptic indication. In some examples, indicator 114 can be a light, such as light emitting diode (LED). In these examples, indicator 114 can include a supporting power source and circuit configured to communicate, for example, with sensor 112 and/or controller 116.

Controller 116 can be a computer or other microelectronic processing system configured to perform analysis on data and signals, as discussed further below. In some examples, sensor 112 and indicator 114 can be electrically or electromagnetically coupled to controller 116, allowing communication therebetween.

Pad 102 can include contact portion 118, which can be the portion of pad 102 configured to interact with a walking surface, such as a floor. Support portion 120 can be a rigid component comprised of plastics, metals, composites, and combinations thereof. Support portion 120 can be configured to support a foot and transfer loads between contact portion 118 and the foot as well as between contact portion 108 and the other components of stabilization device 101. Sensors 122a and 122b can be sensors configured to produce signals as a function of detected conditions. Sensors 122a and 122b can be in communication with controller 116 and/or indicator 114, in some examples.

In operation of some examples, a patient can insert their foot into stabilization device 101, such that their toes extend through toe opening 110. The patient can use straps 106 to secure their foot within stabilization device 101. The patient can then walk using stabilization device 101 as the patient normally would use a shoe, for example. The patient can walk, for example, around a house or on sidewalks and grass surfaces, et cetera.

As the patient walks, sensors 112 and 122a and 122b can detect conditions of the stabilization device, such as forces, stresses, strains, and orientations with respect to gravity. Sensors 112 and 122a and 122b can produce signals as a function of the sensed conditions, which can be transmitted to controller 116. Controller 116 can analyze the signals to determine conditions of stabilization device 101 and the human foot and leg therein.

When controller 116 determines that a condition is outside of an acceptable range, controller 116 can send a signal to indicator 114. For example, controller 116 can determine that an off-axis force is above a maximum acceptable force and can send a signal to indicator 114 to illuminate a red LED. The red LED can serve as an indication to the patient that an undesirable event has occurred, which can help the patient avoid repeating a behavior likely to cause similar events and conditions.

In some examples, where controller 116 detects multiple conditions outside an acceptable range, controller 116 can send a different signal to indicator 114 to indicate that that the patient is repeatedly acting in a way that may be (or already is) dangerous to the patient. For example, the indicator may flash a red LED upon detection of multiple off-axis forces outside an acceptable range. In some other examples, controller 116 may send a signal to a remote device (such as a mobile device), as described below, to instruct the patient's activity decisions.

By notifying the patient of a dangerous or a potentially dangerous condition, stabilization system 100 can help the patient prevent injuries and re-injuries of the foot and distal portions of the patient's tibia and fibula. Further, the notifications can help to detect injuries as soon as they occur, which can minimize the injury, in some cases.

Figure 2:
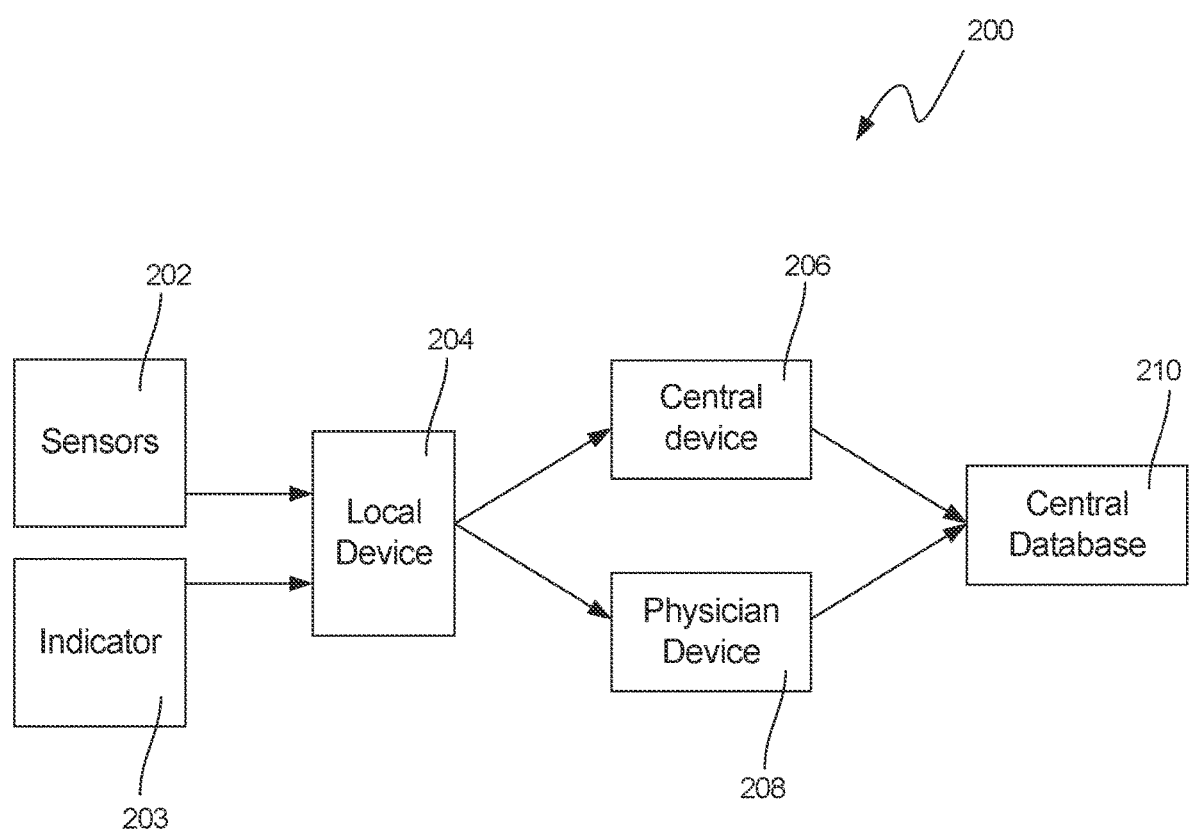
FIG. 2 illustrates a schematic view of a stabilization system, in accordance with at least one example of the present disclosure.

FIG. 2 illustrates a schematic view of stabilization system 200, in accordance with at least one example of the present disclosure. Stabilization system 200 can include sensors 202, local device 204, central device 206, physician device 208, and central database 210. Though not shown, stabilization system 200 can include stabilization device 101 of FIG. 1. Further, components of stabilization system 200 can be mounted to stabilization device 101.

Stabilization system 200 offers the benefit of providing measurement data from a stabilization device that can be used to detect the presence of an injury or conditions likely to cause an injury. Moreover, the data can be sent to multiple devices, such as an external device, a central device, a central device database, and an expert device, to provide detailed and in-depth analysis on the data retrieved, such as comparing the data to data received from other sensors, and analysis performed by experts possessing knowledge not readily available, to determine the probably of an injury, failed equipment, or other problem.

Sensors 202 can be sensors configured to produce a sensor signal as a function of a sensed condition of a stabilization device. Sensors 202 can be a force sensor, a strain sensor, a gyroscope, a displacement sensor, and the like. In some examples, sensors 202 can by multiples of a single type of sensors, such as a plurality of accelerometers. In other examples, sensors 202 can be multiple sensors of different types, such as accelerometers and gyroscopes.

Indicator 203 can be a device configured to produce a visual, audible, or haptic indication. In some examples, indicator 203 can be a light, such as light emitting diode (LED). In some other examples, indicator 203 can be a haptic device, such as an eccentric rotating mass vibration motor (ERM) or a linear resonant actuator (LRA), configured to produce a vibration as a function of a signal. In other examples, indicator 203 can be a speaker. Indicator 203 can be in communication with local device 204 and can be physically mounted to stabilization device 101 in some examples, and can be remote from stabilization device 101 in some other examples.

Local device 204 can be a controller (such as controller 116 of FIG. 1, for example). Local device 204 can be any computing device, such as a handheld computer, for example, a smart phone, a tablet, a laptop, a desktop computer, or any other computing device including a processor and wired or wireless communication capabilities. In some examples, local device 204 can be a microelectronic device contained within stabilization device 101 of FIG. 1, which may include an integrated power source, such as a rechargeable battery. In some examples, controller 204 can include a display, which can be a monitor or other device capable of displaying information received from local device 204.

Local device 204 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Local device 204 can connect to sensors 202, central device 206, physician device 208 and central database 210 (via central device 206 and/or physician device 208). Local device 204 can also connect to an indicator, such indicator 114 of FIG. 1. In some examples, the components of stabilization system 200 can connect via a communication network, which can utilize any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi® or IEEE 802.15.4 family of standards known as ZigBee)), as the personal area network family of standards known as Bluetooth® that are promulgated by the Bluetooth Special Interest Group, peer-to-peer (P2P) networks, among others. The components of stabilization system 200 can also connect via a combination of networks and network types, in some examples.

Central device 206 can be similar to local device 204, but can be located remotely from a patient. For example, central device 206 can be located at a central server operated by experts, such as the producers of stabilization system 200. Similarly, physician device 208 can be similar to local device 204, but can be located remotely from a patient, such as at a physician's office or on a physician's device, such as a smart phone, tablet computer, laptop computer, personal computer, and the like. Central database 210 can be a database for storing measurements and analysis from external device local device 204, central device 206, and physician device 208.

In operation of some examples, sensors 202 can produce signals as a function of detected conditions of a stabilization device, such as stabilization device 101 of FIG. 1. Then, local device 204 can connect to sensors 202. At this time, a communicative link can be confirmed and transmission of power and data can occur between local device 204 and sensors 202. For example, sensor data, such as forces, directions, pressures, stresses, and strains can be transmitted from sensors 202 to local device 204. Local device 204 can perform analysis on the received data and can then transmit results of the analysis along with the data to central device 206 and/or physician device 208. Local device 204 can also send signals to indicator 203 and sensors 202, as necessary. Central device 206 can perform further analysis, before and after communicating with physician device 208. Also, a physician may perform analysis outside of physician device 208, which can then be entered into physician device 208. Thereafter, physician device 208 can then communicate with central device 206 to relay any additional data and/or analysis performed. Each of physician device 208 and central device 206 can connect to central database 210, where data and analyses can be compared to data from other patients to help make determinations, diagnoses, and track patient health and patient activity.

Thereafter, all of the analysis and data derived from central device 206, physician device 208, and central database 210 can be communicated to local device 204, where a user can view the data and analysis (for example in simplified terms) to make a decision regarding the foot or leg on which stabilization system 200 is installed. Similarly, decisions and/or instructions made by experts and/or physicians can be communicated to local device 204 and thereafter to the patient.

Analysis performed by local device 204, central device 206, and/or physician device 210 can determine whether conditions experienced by stabilization device 201 may have caused (or are likely to cause) injury or re-injury to the foot of the patient. Other analysis such as determining remaining capacitor health, signal strength, and component functionality may also be performed by these devices.

Figure 3A:
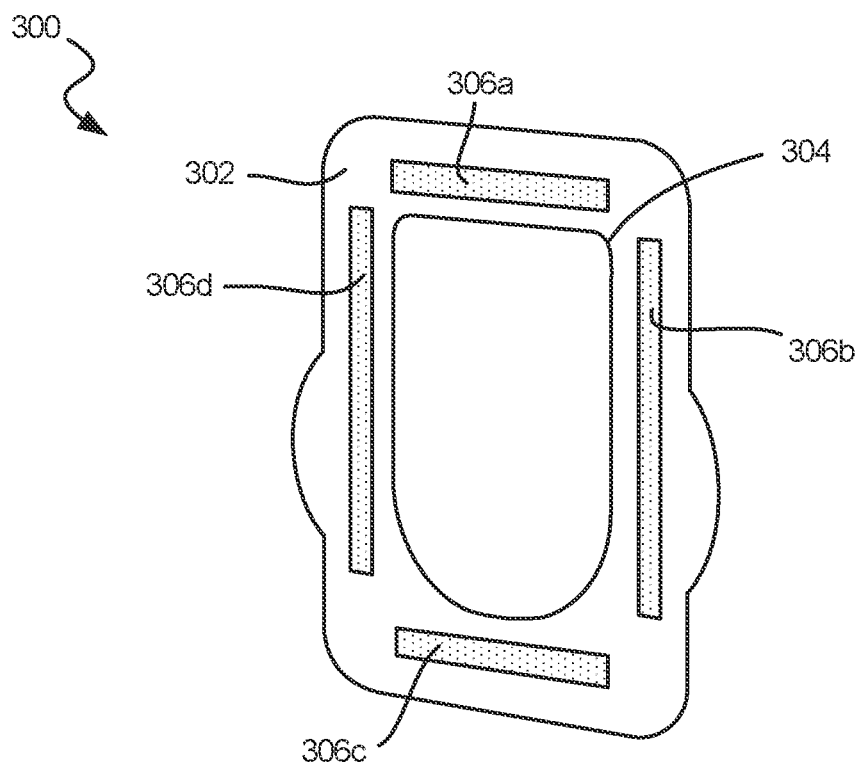
FIG. 3A illustrates a perspective view of a portion of a stabilization system, in accordance with at least one example of the present disclosure.
Figure 3B:
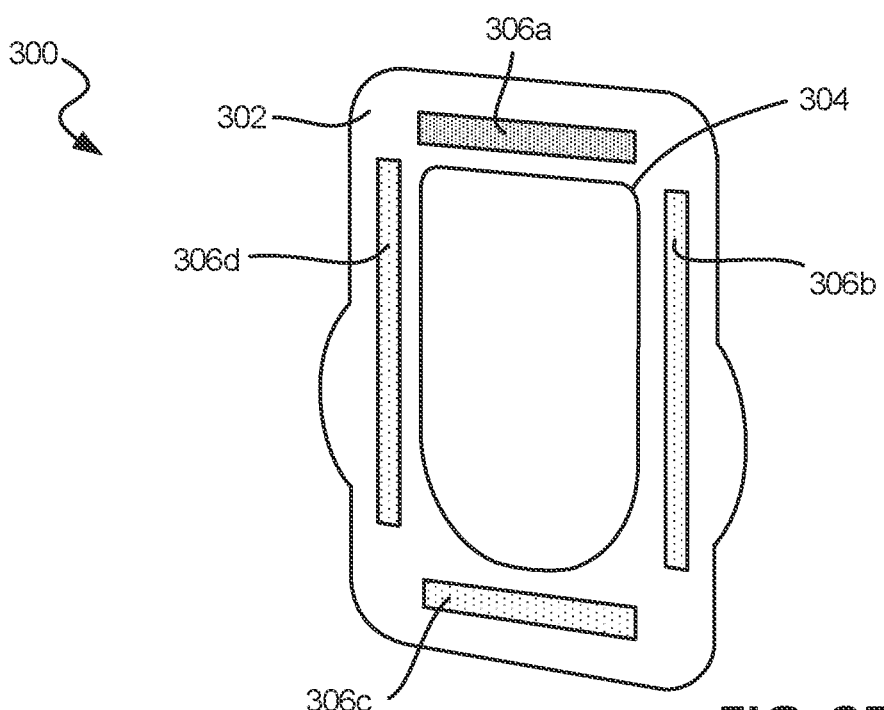
FIG. 3B illustrates a perspective view of a portion of a stabilization system, in accordance with at least one example of the present disclosure.

FIG. 3A illustrates a perspective view of a portion of stabilization system 300, in accordance with at least one example of the present disclosure. FIG. 3B illustrates a perspective view of a portion of stabilization system 300, in accordance with at least one example of the present disclosure. FIGS. 3A and 3B are discussed below concurrently.

Either of stabilization systems 100 or 200 can include an indicator, as discussed above. As discussed below, a stabilization system can further include a plate, such as plate 302 of FIGS. 3A and 3B. Plate 302 can function as a support for a stabilization system, as discussed below, or can function only as an indicator.

In each example, plate 302 can be a rigid member comprised of materials such as plastics, metals, composites, and combinations thereof. Central opening 304 can be sized to receive, for example a foot of the patient therethrough. Plate 302 can be secured to stabilization device 100 in some examples, and can be integrated into the stabilization device of FIG. 4 in other examples.

In some examples, plate 302 can include central opening 304 and indicators 306a-306d disposed around a periphery of central opening 304. Each of indicators 306a-306d can be an individual indicator in communication with a controller, such as controller 116 of FIG. 1 or local device 204 of FIG. 2. In some examples, each of indicators 306a-306d can be an LED.

In operation of some examples, a controller can send a signal to indicators 306a-306d to indicate a condition has been detected. For example, controller 116 can send signals to activate a green LED of one or more of indicators 306a-306d for each step taken by a patient where the conditions detected are within an acceptable range and can a signal to activate a red LED for one or more of indicators 306a-306d when a condition detected is outside of an acceptable range. In some examples, the LED activated can indicate from where the condition was detected. For example, indicator 306 can display a red LED when a problematic condition is detected at an anterior portion of the stabilization device. Plate 302 can therefore help provide notice to a patient of potentially problematic conditions or potential sources of injuries and their locations.

Figure 4:
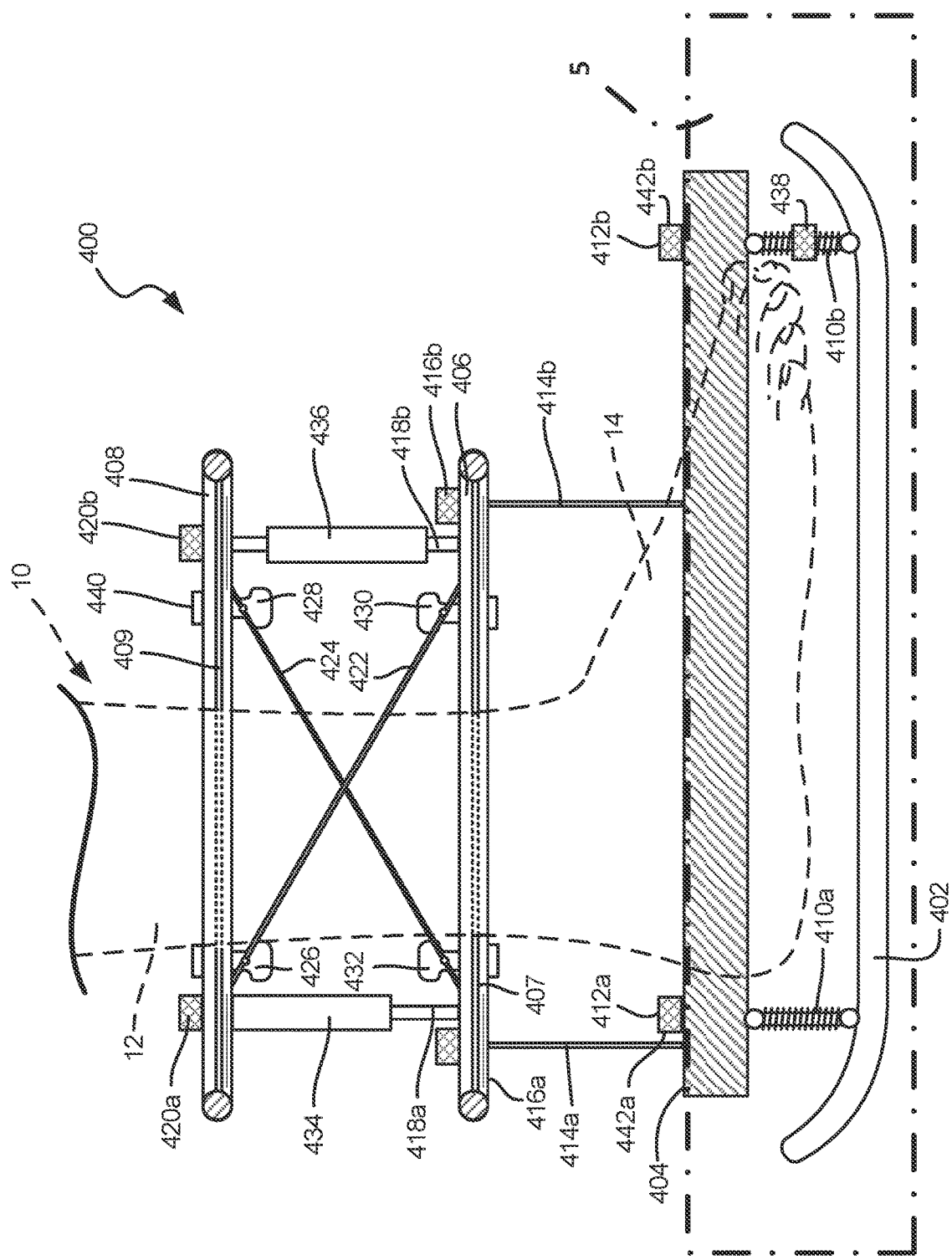
FIG. 4 illustrates an elevation view from a lateral perspective of a stabilization system, in accordance with at least one example of the present disclosure.

FIG. 4 illustrates an elevation view from a lateral perspective of stabilization system 400, in accordance with at least one example of the present disclosure. Stabilization system 400 can include pad 402, plate 404, distal ring 406, distal pin 407, proximal ring 408, proximal pin 409, pad struts 410a and 410b, pad adjustments 412a and 412b, distal struts 414a and 414b, distal adjustments 416a and 416b, proximal struts 418a and 418b, proximal adjustments 420a and 420b, wires 422 and 424, wire supports 426, 428, 430, and 432, displacement sensor 434, film sensor 436, strain sensor 438, and accelerometer 440. Also shown in FIG. 4 is right leg 10, which includes distal portion 12 and foot 14. As discussed further below, distal portion 12 can include a tibia and a fibula.

Pad adjustments 412a and 412b, distal adjustments 416a and 416b, and proximal adjustments 420a and 420b can be fasteners (such as threaded nuts or bolts, in some examples) engageable with struts. The adjustments can be adjustable to adjust an amount of a strut passing therethrough. In this way, the effective height of each strut can be adjusted between its connecting members.

Pins 407 and 409, can be rigid members configured to couple to rings 406 and 408. Pins 407 and 409 can be Schanz pins, in some examples, configured to pass through distal portion 12 of leg 10 to secure rings 406 and 408, respectively, to leg 10. Pins 407 and 409 can be comprised of biocompatible materials such as stainless steel alloys, titanium, titanium alloys, cobalt chromium alloys, and the like. Pin supports can secure pins 407 and 409 to rings 406 and 408, respectively, in some examples.

Wires 422 and 424 can be semi-rigid members coupleable to rings 406 and 408. Wires 422 and 424 can be comprised of materials such as steel and steel alloys, titanium and titanium alloys, aluminum and aluminum alloys, plastics, composites, combinations thereof, and the like. Wire supports 426, 428, 430, and 432 can be adjustable fasteners configured to secure wires 422 and 424 to rings 406 and 408 in some examples. In some examples, wire supports 426-432 can each include sensors, such as accelerometers, displacement sensors, strain sensors, and the like.

Pad struts 410a and 410b, distal struts 414a and 414b, and proximal struts 418a and 418b can be rigid structural components configured to transfer tensile loads, compression loads, and moments between components connected to the struts. The struts can be comprised of materials such as metals, plastics, combinations thereof, and the like.

Pad 402 can be similar to pad 102 of FIG. 1, except that pad 402 can be mounted to plate 404 using struts 410a and 410b. Plate 404 can be a rigid member comprised of materials such as metals, plastics, composites, combinations thereof, and the like. Plate 404 can be coupled to foot 14, in some examples, using pins (not shown). Pad struts 410a and 410b can be secured to pad 402 through a threaded engagement, in some examples, and can be secured in other manners, such as welded, in other examples. Pad struts 410a and 410b can pass through plate 404 in some examples and can engage pad adjustments 412a and 412b, which can threadably engage pad struts 410a and 410b to secure pad struts 410a and 410b and therefore pad 402 to plate 404.

Distal ring 406 and proximal ring 408 can be rigid members comprised of materials such as metals, plastics, composites, combinations thereof, and the like. Distal ring 406 and proximal ring 408 can be sized to surround a distal portion 12 of leg 10. In some examples, distal ring 406 can be coupled to plate 404 by distal struts 414a and 414b, which, in some examples, can pass through distal ring 406 and can be adjustably secured to distal adjustments 416a and 416b, respectively. Similarly, proximal ring 408 can be coupled to distal ring 406 by proximal struts 418a and 418b, which, in some examples, can pass through proximal ring 408 and can be adjustably secured to proximal adjustments 420a and 420b, respectively. Though only two rings are shown (distal ring 406 and proximal ring 408) more rings, such as 3, 4, 5, and the like can be used. Similarly, one ring (either distal ring 406 or proximal ring 408) can be used in some examples.

Displacement sensor 434 can be a linear variable differential transformer (LVDT) or can be a receiving tube that includes, for example, a Hall Effect sensor together with the tube comprising a displacement sensor. Displacement sensor 434 can be configured to produce a displacement signal as a function of the length of proximal strut 418a between proximal ring 408 and distal ring 406.

Film sensor 436 can be, for example, a piezoelectric film sensor configured to produce a signal as a function of a sensed condition of film sensor 436. Because film sensor 436 can be mounted to (or wrapped around) proximal strut 418b, film sensor 436 can produce a signal as a function of a sensed condition of proximal strut 418b. Film sensor 436 can be configured to produce a signal as a function of a sensed pressure, strain, force, temperature, or acceleration.

Strain sensor 438 can be mounted to strut 410b, in some examples, and can be a strain gauge configured to produce a strain signal as a function of a measured strain. Strain sensor 438 can be a foil strain gauge in some examples. Accelerometer 440 can be secured to proximal ring 408 and can be an accelerometer configured to produce an acceleration signal as a function of measured acceleration relative to accelerometer 440. In some examples, accelerometer 440 can include a gyroscope configured to produce a signal as a function of a measured orientation relative to the direction of the force gravity. In some examples, accelerometer 440 can produce one signal that includes acceleration and orientation of the acceleration relative to the direction of the force gravity.

In operation of some examples, stabilization system 400 can be secured to foot 14 and distal portion 12 of leg 10 and the structural components of stabilization system 400 can be secured to each other as described above. When installed, stabilization system 400 can allow a patient to walk using right leg 10 such that pad 402 contacts a walking surface, transferring forces between the walking surface and plate 404 via pad struts 410a and 410b. Plate 404 can transmit received forces and moments to distal ring 406 via distal struts 414a and 414b. Distal ring 406 can transmit forces and moments to distal portion 12 of leg 10 via distal pin 407 and can transmit forces and moments to proximal ring 408 via proximal struts 418a and 418b and pins 422 and 424. Proximal ring 408 can transfer forces and moments to leg 10 via proximal pin 409. As pad 402 contacts a walking surface, the transmitted forces, moments, stresses, strains, and orientation can be measured via the sensors of stabilization system 400.

In one example, strain sensor 438 can measure strain applied to strut 410b. Strain sensor 438 can produce a strain signal as a function of the measured strain and the strain signal can be delivered to a controller, for example local device 204 of FIG. 2. In some examples, strut 410a can also include strain sensor 438 configured to measure strain on strut 410a. Further, more than two struts, such as 3, 4, 5, 6, 7, 8, and the like, can be used, and in some examples, each strut can include a sensor that can be in communication with a controller. The controller can analyze the signal or signals received from the strain sensors to determine strain placed on one or more of the struts, such as struts 410a and 410b. When the controller detects a strain that is above an acceptable strain (such as a strain that indicates a bending moment higher than is desirable), controller can send a signal to an indicator or to another device to alert that a problematic (or potentially problematic) condition has occurred. For example, a large strain may indicate the occurrence of a high off-axis load that can be damaging to the pins connecting to leg 10 and can be damaging to the tissues and bones of leg 10. A relatively large strain may also indicate a failure or probable failure of one of struts 410a and 410b. Similarly, a prolonged detection of a strain may indicate a failure or deformation of one or more of struts 410a and 410b. Further, a repeated detection of a strain can indicate a problematic impact angle or other gait irregularity.

In another example, accelerometer 440 can produce an acceleration signal as a function of an acceleration of stabilization system 400 as pad 402 contacts the walking surface and as stabilization system 400 is generally moved through space. The acceleration signal can be transmitted to a controller (such as local device 204) where the controller can determine when an acceleration is higher than an allowable acceleration. In some examples, the controller can be notified of a mass and can solve for a force from the measured acceleration. The controller can use the acceleration and/or force to determine whether conditions of gait and impacts are acceptable. When the conditions are not acceptable, such as when an acceleration is higher than desirable, the controller can send a signal to an indicator or to another controller or device to indicate or display such information.

In some examples, pad adjustments 412a and 412b can include load cells 442a and 442b, which can produce a signal as a function of a measured load applied by struts 410a and 410b to plate 404. Load cells 442a and 442b can produce a force signal as a function of the detected loads, which can be transmitted to a controller (such as local device 204 of FIG. 2).

In some examples, the controller can use the force signal from load cells 442a and/or 442b and the accelerometer signal to calculate a mass applied to struts 410a and 410b, which can be used (for example by comparing the calculated mass to mass inputs) to determine whether the external fixator is properly or improperly loaded during steps taken by the patient.

In another example, displacement sensor 434 can produce a displacement signal as a function of measured displacement of proximal strut 418a (or distance between distal ring 406 and proximal ring 408) at proximal strut 418a. The displacement signal can be transmitted from displacement sensor 434 to a controller, such as local device 204 of FIG. 2, for example. In some examples, the controller can send a signal to a display, indication device, or other device, such as a mobile device to indicate the distance between proximal ring 408 and distal ring 406 at proximal strut 418a. When adjustments to proximal struts 418a and 418b are required, a patient can use proximal adjustments 420a and 420b to adjust the distance between proximal ring 408 and distal ring 406. During this procedure, the patient can receive feedback from displacement sensor 434 and the controller (and a display or indicator). For example, an indicator can flash green when further adjustment is required, can flash yellow when adjustment is correct and can adjust red when the strut has been adjusted too far in one direction. In these examples, the required adjustments can be sent to the local device from a central device or a physician device (such as central device 206 or physician device 208 of FIG. 2). In some examples, struts and/or adjustments can be colored to simplify instructions for making adjustments. Further, the results of the adjustment can be stored by the local device and communicated back to the central device and/or physician device.

In another example, a display can show a visual representation of the strut and can indicate how much adjustment is to be made. In some example, both of struts 418a and 418b can include displacement sensors, and in other examples, all of the struts between proximal ring 408 and distal ring 406 can include displacement sensors. Further, one or more of distal struts 414a and 414b can also include a displacement sensor, which can be used for adjustments as described above with respect to proximal struts 418a and 418b and displacement sensor 434.

In another example, film sensor 436 can produce a signal as a function of a measured condition of strut 418b, such as a function of a sensed pressure, strain, force, temperature, or acceleration. In each of these examples, film sensor 436 can transmit the signal to the controller for analysis of the condition.

Though there are two of each struts shown in FIG. 4 more struts can be used as required to transmit forces and moments between components of stabilization system 400. Also, though the sensors of stabilization system 400 are shown as being coupled to specific components of stabilization system 400, the sensors can be interchanged and multiples of each type of sensor can be used.

Figure 5:
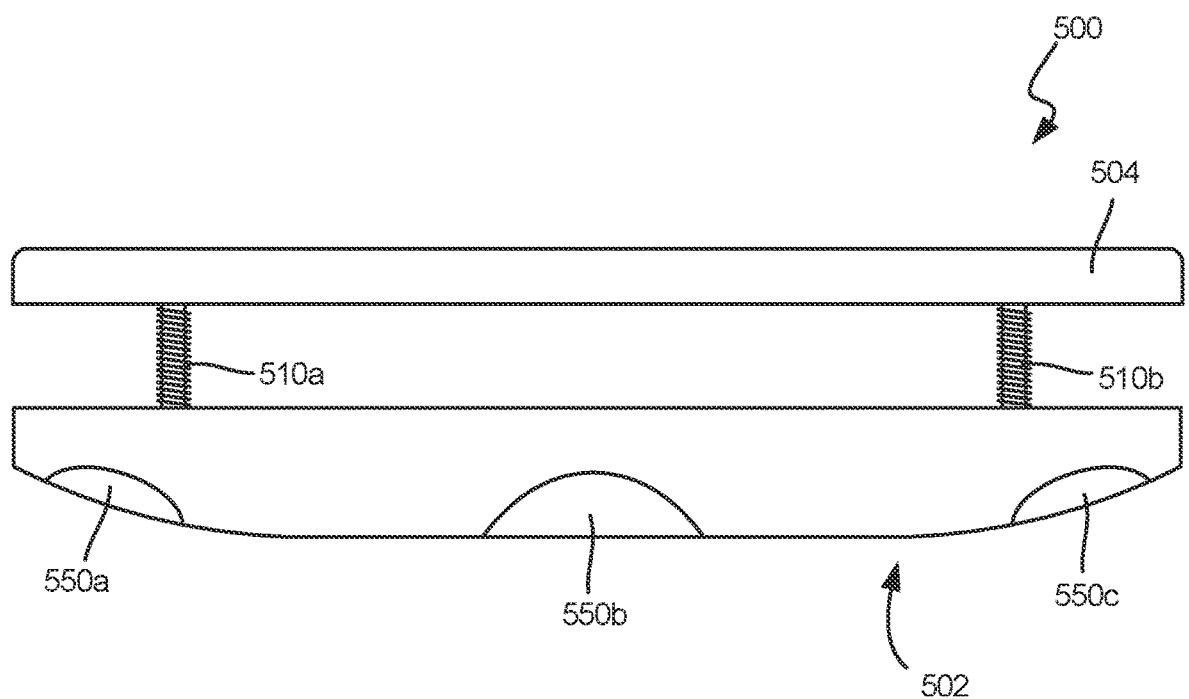
FIG. 5 illustrates an elevation view from a lateral perspective of a portion of a stabilization system, in accordance with at least one example of the present disclosure.

FIG. 5 illustrates an elevation view from a lateral perspective of a portion of stabilization system 500, in accordance with at least one example of the present disclosure. Stabilization system 500 can include pad 502, plate 504, struts 510a and 510b, and sensors 550a, 550b, and 550c.

The components of stabilization system 500 can be similar to those of stabilization system 300 of FIG. 3, except that pad 502 can include sensors 550a, 550b, and 550c. Sensors 550a-550c can be of several types of sensors described above, such as accelerometers, load cells, strain sensors, and piezoelectric film. Each of sensors 550a-550c can produce a sensor signal as a function of a measured condition of pad 502. The signals can be transmitted to a controller, such as local device 204 of FIG. 2, where the controller can analyze the signals to determine conditions of stabilization system 500.

In one example, sensors 550a-550c can be load cells, where each of sensors 550a-550c can measure a load or force on a different portion of pad 502. In this example, each of sensors 550a-550c can produce a signal as a function of the measured force, where each signal can be transmitted to the controller. The controller can use one or more of the signals to determine load distribution on pad 502 during impact between pad 502 and walking surfaces. The controller can determine (and produce a signal to be transmitted to an indicator or device) when the loads are improperly distributed or when any of the detected loads are above an acceptable maximum load. Detecting improper loading can help prevent injury or re-injury to a patient and can help detect injuries early after occurrence.

Figure 6:
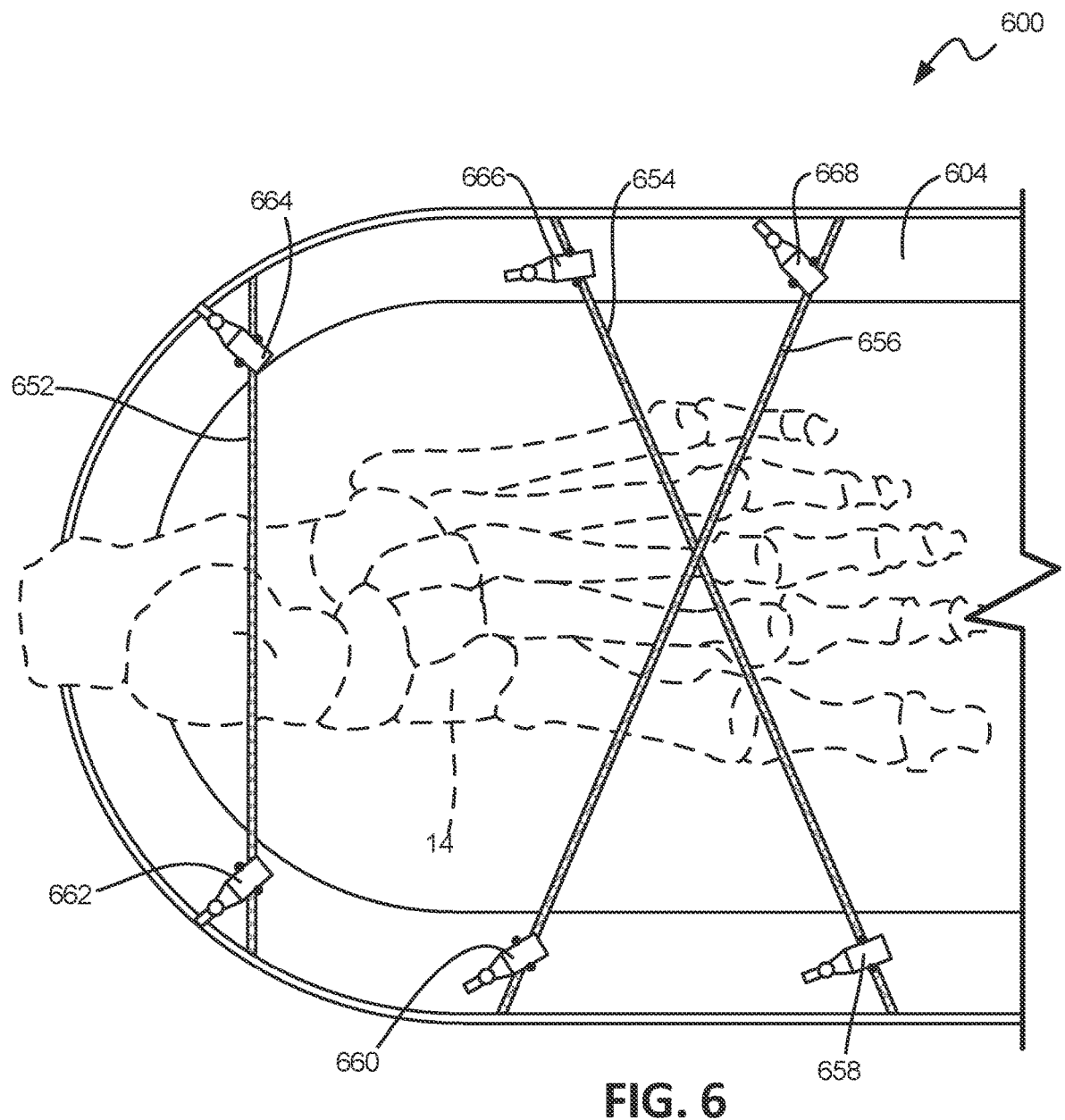
FIG. 6 illustrates an elevation top view of a portion of a stabilization system, in accordance with at least one example of the present disclosure.

FIG. 6 illustrates an elevation top view of a portion of stabilization system 600, in accordance with at least one example of the present disclosure. Stabilization system 600 can include plate 604, wires 652, 654, and 656, and wire bolts 658, 660, 662, 664, 666, and 668. Each of wire bolts can include an integrated sensor. Also shown in FIG. 6 is foot 14.

Plate 604 can be similar to plate 404 described above with respect to FIG. 4. Wires 652-656 can be similar to wires 422 and 424 described above with respect to FIG. 4, except that wires 652-656 can cross over foot 14 medially to laterally and can connect to plate 604 at multiple locations via wire bolts 658-668. Wire bolts 658-656 can be bolts configured to adjustably secure wires 652-656 to plate 604. Wire bolts 658-656 can be a screw and bolt, can be spring toggles, bores and set screws, and the like. In some examples, wire bolts 658-656 can each include a sensor, which can be configured to measure, force, strain, temperature, acceleration, and the like.

In operation of one example, where each of wire bolts 658-656 includes a force sensor, the force sensors can transmit force signals to a controller. The controller can store values of forces on each of wire bolts 658-656 and can transmit a signal to an indicator or remote device when the force on any of wire bolts 658-656 is larger than an acceptable force. Similarly, the controller can transmit a signal to an indicator or remote device when the force on any of wire bolts 658-656 deviates from a typical force applied to any of wire bolts 658-656. For example, a small force may indicate that a wire is broken.

Figure 7:
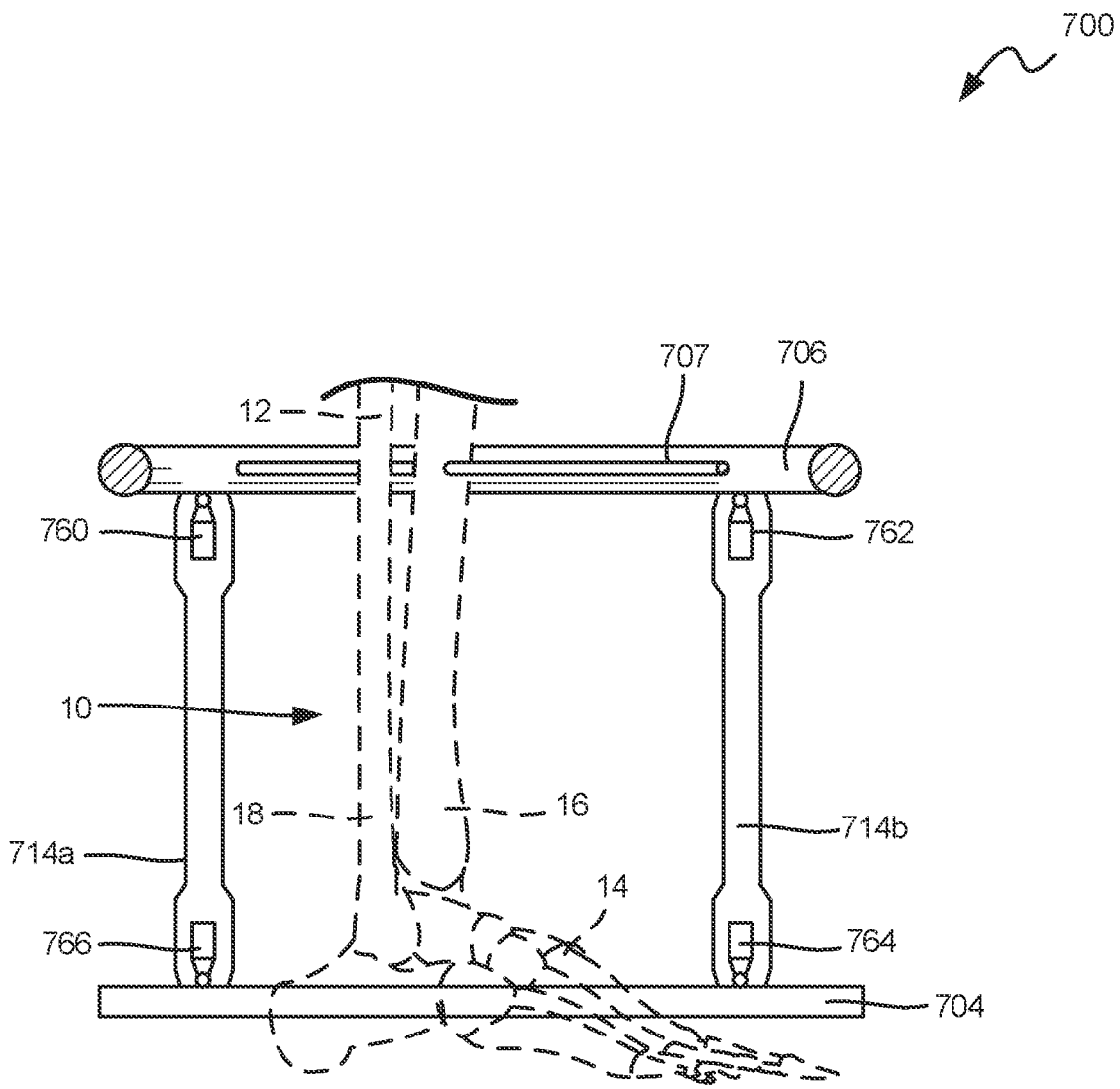
FIG. 7 illustrates an elevation view from a lateral perspective of a stabilization system, in accordance with at least one example of the present disclosure.

FIG. 7 illustrates an elevation view from a lateral perspective of stabilization system 700, in accordance with at least one example of the present disclosure. Stabilization system 700 can include plate 704, distal ring 706, distal pin 707, distal struts 714a and 714b, and strut sensors 760, 762, 764, and 766. Also shown in FIG. 7 are leg 10, which includes distal portion 12, and foot 14. Distal portion 12 can include tibia 16 and fibula 18.

Stabilization system 700 can be similar to stabilization system 400 of FIG. 4, however, stabilization system 700 shows how distal pin 707 can pass through tibia 16, being secured to distal ring 706 at two locations, fixing the position of distal ring 706 relative to tibia 16 and therefore leg 10. Stabilization system 700 can also differ in that each of distal struts 714a and 714b can include a sensor at each connection point between distal struts 714a and 714b and plate 704 and distal ring 706. As discussed above, each of strut sensors 760, 762, 764, and 766 can be a variety of sensors configured to produce signals as a function of measured conditions.

In operation of one example, strut sensors 760-766 can be strain sensors configured to transmit a strain signal to a controller as a function of measured strain. The controller can use the strains to determine when loading is off-axis and/or when the loading is likely to cause failure of a strut. Similarly, the strain can be used to determine a moment of each strut, which can be used for similar calculations.

Figure 8:
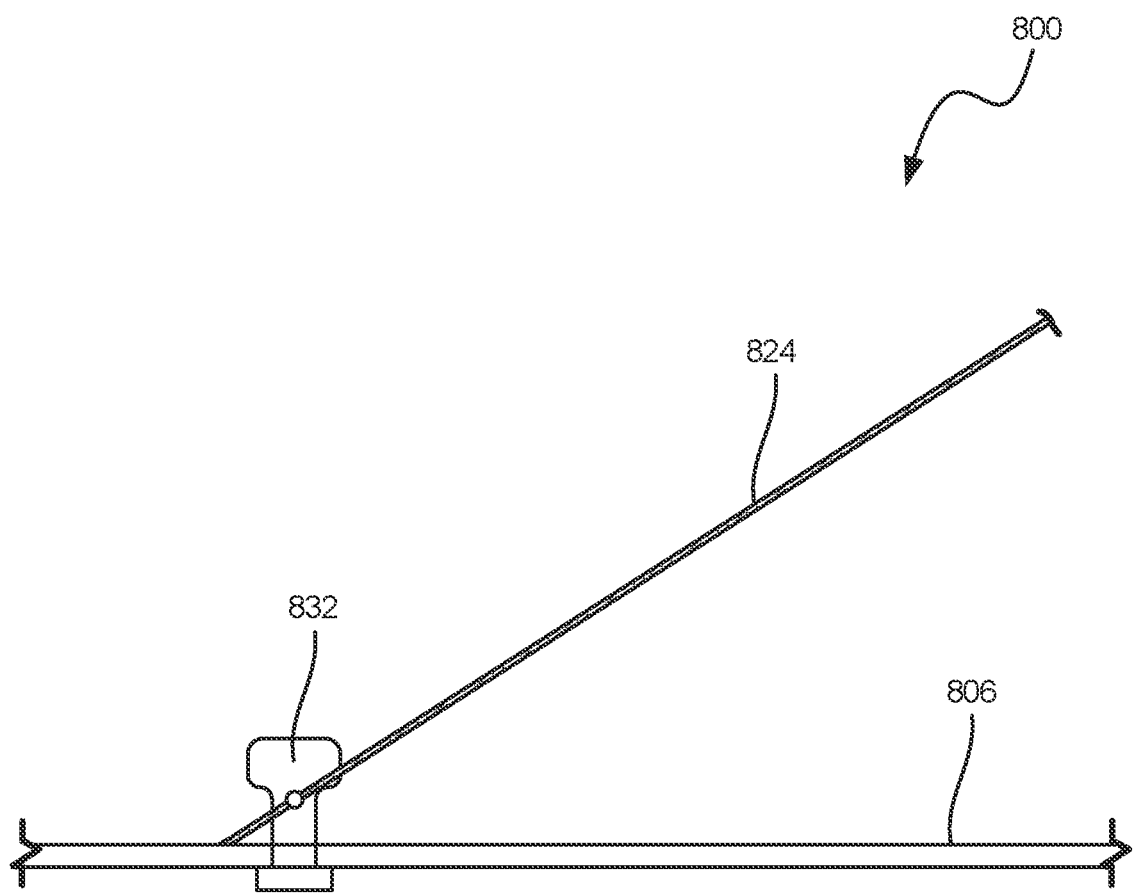
FIG. 8 illustrates elevation view of a stabilization system, in accordance with at least one example of the present disclosure.

FIG. 8 illustrates elevation view of stabilization system 800, in accordance with at least one example of the present disclosure. Stabilization system 800 can include distal plate 806, wire 824, and wire bolt 832. Stabilization system 800 can be similar to stabilization system 400 described with respect to FIG. 4 above, except that stabilization system shows how wire bolt 832 can secure wire 824 to distal ring 806.

Figure 9:
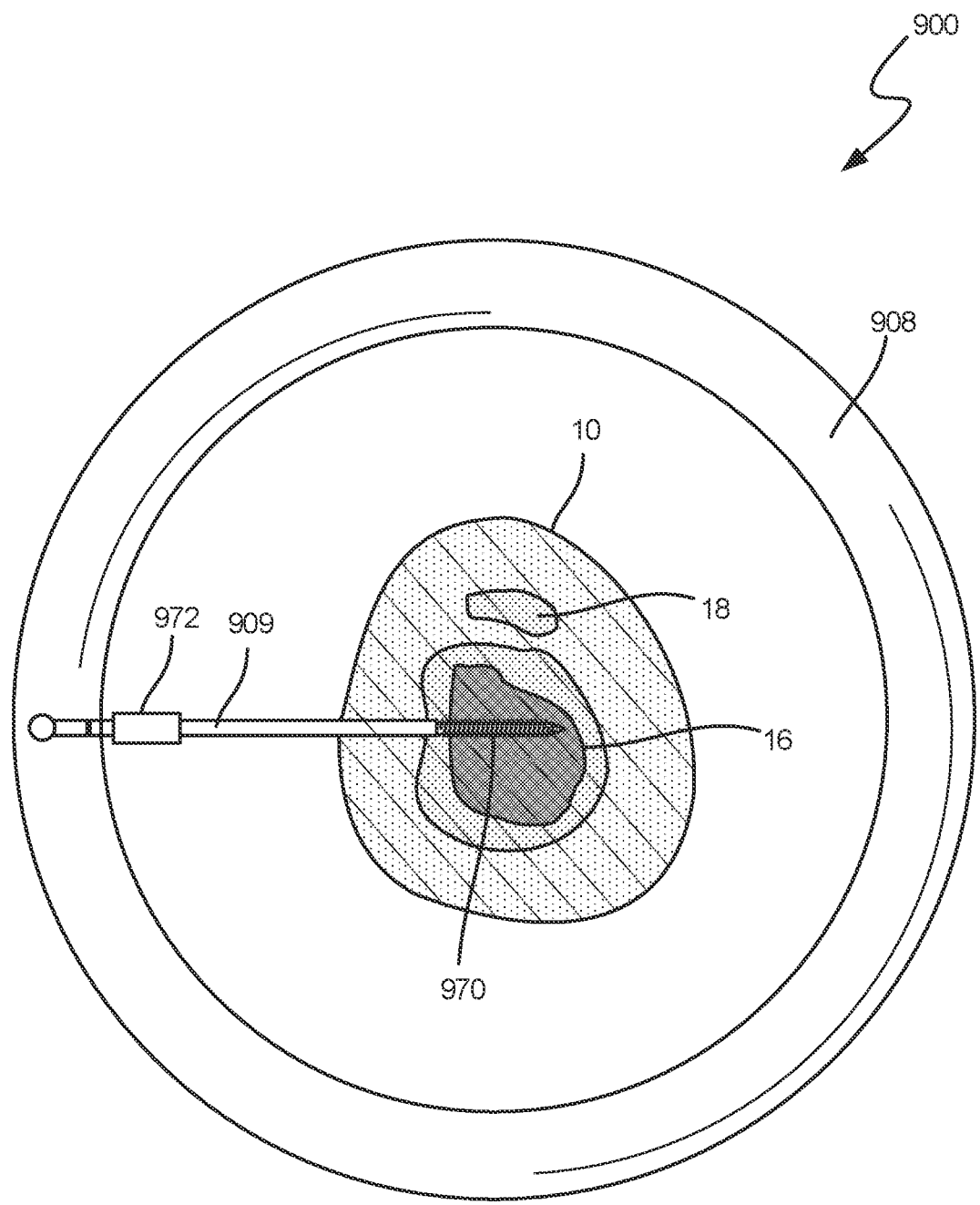
FIG. 9 illustrates a top cross sectional view of a portion of a stabilization system, in accordance with at least one example of the present disclosure.

FIG. 9 illustrates a top cross sectional view of a portion of stabilization system 900, in accordance with at least one example of the present disclosure. Stabilization system 900 can include proximal ring 908 and proximal pin 909. Proximal pin can include distal threaded portion 970 and sensor 972. Also shown in FIG. 9 is leg 10, which can include tibia 16 and fibula 18.

Stabilization system 900 can be similar to stabilization system 400 described above with respect to FIG. 4, except that stabilization system 900 shows how threaded portion 970 of proximal pin 909 (which can be a Schanz pin, in some examples), can be threaded into tibia 16 of leg 10 to secure proximal pin 909 and therefore proximal ring 908 to tibia 16. Stabilization system 900 further illustrates sensor 972 disposed at the connection between proximal pin 909 and proximal ring 908.

In operation of some examples, sensor 972 can be a piezoelectric film sensor configured to produce a signal as a function of a measured condition of pin 909, which can be transmitted to a controller. In one example, the controller can send a signal to an indicator (or another device) when the controller determines that a condition of pin 909 is problematic, such as when a measured strain is above an allowable maximum strain, which can indicate potential damage to pin 909 and/or tibia 16. This can help prevent damage: to tibia 16 and can help to detect injuries to tibia 16.

Figure 10:
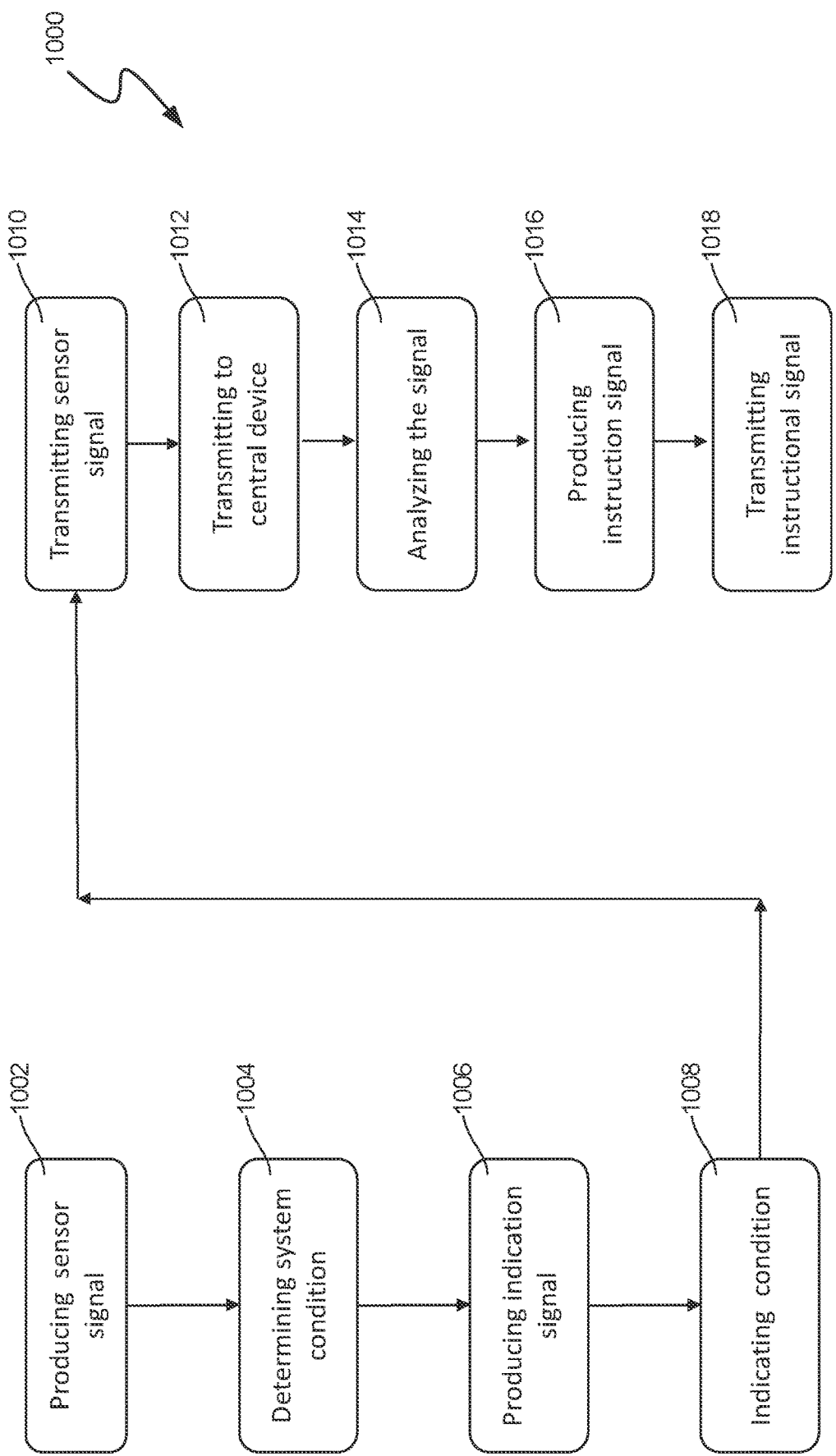
FIG. 10 illustrates a flow chart view of a method, in accordance with at least one example of the present disclosure.

FIG. 10 shows a flow chart of using the devices and systems described above, in accordance with at least one example of this disclosure. The steps or operations of the method of FIG. 10 are illustrated in a particular order for convenience and clarity. Many of the discussed operations can be performed in a different sequence or in parallel, and some operations may be excluded, without materially impacting other operations. The method of FIG. 10, as discussed, includes operations that may be performed by multiple different actors, devices, and/or systems. It is understood that subsets of the operations discussed in the method of FIG. 10 that are attributable to a single actor, device, or system could be considered a separate standalone process or method.

In operation of one example, method 1000 can begin with step 1002, where a sensor, such as sensor 112 of FIG. 1A, can produce a sensor signal, which can also be transmitted to a controller, such as controller 116 of FIG. 1 in step 1002. At step 1004 the controller can determine a condition of the stabilization system as a function of the condition. For example, as a function of a force signal from transmitted to the controller from a force sensor, the controller can determine a force at the force sensor.

At step 1006, the controller can produce an indication signal when the determined condition is outside of a desirable range, for example, when a force is too large (indicating a potential injury or component break) or when a force is too small (indicating an already broken component) when conditions of other sensors indicate that movement of the patient. The indication signal can be transmitted to an indicator (such as indicator 114 of FIG. 1) or another device, such as central device 206 and/or physician device 208. Further, in some examples, the controller can also be a device capable of displaying an indication to the patient, which can occur a step 1008.

At steps 1010 and 1012, the sensor signal can be further transmitted to another device, such as central device 206 and physician device 208, respectively. At step 1014 the central device 206 and/or physician device 208 can analyze the signal. Also, at step 1014 an expert and/or a physician can analyze the signal or data in lieu of or in addition to central device 206 and/or physician device 208. At step 1016, as a result of the analysis, instructions from an expert, physician, central device 206, and/or physician device 208 can be produced and can be transmitted back to local device 204 (or controller 116 and in some examples indicator 114 at step 1018. The patient can then receive the instructions and adjust the stabilization system per the instructions, can adjust his or her activities, or can make plans to visit a physician, if required. These steps can prevent unnecessary trips to see a physician and can indicate when a trip to the physician is required.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A stabilization device coup able to a human foot, the stabilization device comprising:
   a body configured to be coupled to a human foot;
   a pad coupleable to a distal portion of the body, the pad configured to interface with a walking surface; and
   a sensor securable to one of the body and the pad, the sensor configured to produce a sensor signal as a function of a sensed condition of the stabilization device;
   a pin configured to pass through a human tibia;
   a ring fixator securable to the human tibia by the pin;
   a foot plate disposable around a periphery of the human foot above the pad;
   a rod coupleable to the foot plate and to the pad;
   a strut configured to couple the foot plate to the ring fixator; and
   a wire securable to a medial portion of the foot plate and a lateral portion of the foot plate;
   a strut sensor coupleable to the strut and configured to produce a strut sensor signal as a function of a condition of the strut; and a foot plate sensor coupleable to the wire and configured to produce a foot plate sensor signal as a function of a condition of the foot plate.

2. The stabilization device of claim 1, further comprising:
a pad sensor embedded within the pad and configured to produce a pad sensor signal as a function of a sensed condition of the pad.

3. The stabilization device of claim 2, wherein the pad sensor is one of an accelerometer, a force sensor, and a strain sensor.

4. The stabilization device of claim 1, further comprising:
an indicator securable to one of the body and the pad, the indicator configured to produce a visual indication as a function of the sensor signal.

5. The stabilization device of claim 1, the body further comprising:
a second pin configured to pass through the human tibia;
a second ring fixator securable to the human tibia by the second pin;
a second wire securable to the ring fixator and the second ring fixator;
a ring fixator sensor coupleable to the second wire and configured to produce a ring fixator sensor signal as a function of a condition of one or more of the ring fixator; the second ring fixator, and the second wire.

* * * * *

UNITED STATES PATENT AND TRADEMARK OFFICE
CERTIFICATE OF CORRECTION

PATENT NO. : 11,419,748 B2
APPLICATION NO. : 16/038840
DATED : August 23, 2022
INVENTOR(S) : Zelen et al.

It is certified that error appears in the above-identified patent and that said Letters Patent is hereby corrected as shown below:

In the Claims

In Column 16, Line 47, in Claim 1, delete "coup able" and insert --coupleable-- therefor In Column 17, Line 25, in Claim 5, delete "fixator;" and insert --fixator,-- therefor Signed and Sealed this
Thirtieth Day of May, 2023

Katherine Kelly Vidal
*Director of the United States Patent and Trademark Office*